United States Patent [19]

Schwartz

[11] Patent Number: 4,837,404

[45] Date of Patent: Jun. 6, 1989

[54] PROCESS FOR THE PREPARATION OF OXY-DIPHTHALIC ANHYDRIDES

[75] Inventor: Willis T. Schwartz, Grand Island, N.Y.

[73] Assignee: Occidental Chemical Corporation, Niagara Falls, N.Y.

[21] Appl. No.: 88,325

[22] Filed: Aug. 24, 1987

[51] Int. Cl.$^4$ ............................................. C07D 307/89
[52] U.S. Cl. ..................................................... 549/241
[58] Field of Search ......................................... 549/241

[56] References Cited

U.S. PATENT DOCUMENTS 3,992,407 11/1976 Markezich ...................... 548/476 X
4,697,023 9/1987 Schwartz et al. ................... 549/241

OTHER PUBLICATIONS

Solomons, Fundamentals of Organic Chemistry, 2nd Ed, John Wiley and Sons, New York (1986), p. 552.

*Primary Examiner*—Richard L. Raymond
*Attorney, Agent, or Firm*—James F. Tao; Arthur S. Cookfair

[57] ABSTRACT

Oxy-diphthalic anhydrides are prepared by reacting a halophthalic anhydride with an hydroxyphthalic anhydride in a polar aprotic solvent and in the presence of an alkali metal compound such as KF, CsF or $K_2CO_3$.

19 Claims, No Drawings

PROCESS FOR THE PREPARATION OF OXY-DIPHTHALIC ANHYDRIDES

BACKGROUND OF THE INVENTION

This invention relates to a method for the preparation of oxy-diphthalic anhydrides. The products are useful chemical intermediates for the further preparation of various compounds such as the corresponding dicarboxylic acids and the various derivatives thereof, including for example, the salts, esters, acyl halides, amides, imides and the like. The oxy-diphthalic anhydrides are particularly useful as monomers in the preparation of polyimides, for example by polycondensation with a suitable diamine, such as ethylenediamine or phenylenediamine.

Various methods for the preparation of oxy-diphthalic anhydrides have been described in the chemical literature. One such method, shown to be useful in the preparation of oxy-diphthalic acids and anhydrides, involves the oxidation of tetramethyl diphenyl ethers. See Kolesnikov, G. S. et al *Vysokomol. Soyed, A9,* 612–18 (1967); Marvel, C. S. et al, *J. Am. Chem. Soc.* 80. 1197 (1958); and Latrova, Z. N. et al. *Volokna Sin. Polim.,* 15–24 (1970).

Three Japanese patents assigned to Mitsui Toatsu Chemicals, Inc. describe preparations based on reactions of substituted phthalic anhydrides. Japanese Patent Document No. 80/136, 246 (Chem. Abst. 95:42680) teaches the coupling of 4-nitrophthalic anhydride in the presence of sodium nitrite or potassium nitrate to form oxy-diphthalic oxy-diphthalic anhydride. Japanese Patent Document No. 80/122, 738 (Chem. Abst. 94:83799) discloses the reaction of 4-halophthalic acid or anhydride with an alkali metal hydroxide to yield oxy-diphthalic anhydride. In Japanese Patent Document No. 80/27, 343 (Chem. Abstr. 94:191942) the reaction of 4-halo-phthalic anhydride, Na$_2$CO$_3$ and NaNO$_2$ in dimethyl sulfoxide to form 4,4'-dihydroxydi- phthalylic anhydride is described.

German Patent No. 2,416,594 (1975) discloses the coupling of 3-nitrophthalic anhydride in the presence of metal nitrites, such as sodium nitrite to form oxy-diphthalic anhydride.

Markezich, R. L. and Zamek, O. S. *J. Org. Chem.* 42, 3431 (1977) describe reaction of 4-nitrophthalimide with potassium fluoride in dimethylsulfoxide to form the corresponding oxy-diphthalimide which may be converted by hydrolysis to form the acid and ring closure to form the dianhydride.

SUMMARY OF THE INVENTION

It has now been found that diphthalic ether dianhydrides of the formula

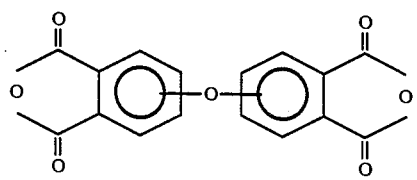

can be prepared by reacting a halo-phthalic anhydride of the formula

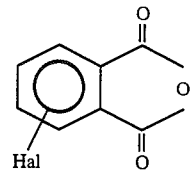

where Hal is F, Cl, Br or I, with an hydroxyphthalic anhydride of the formula

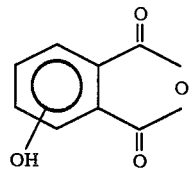

in the presence of a polar, aprotic solvent and an alkali metal compound selected from the group consisting of KF, CsF and K$_2$CO$_3$.

In the process of the invention, the ether bridge is formed at the site of the halo- and hydroxy-substituents on the phthalic anhydride reactants. Thus, when the substituents of both reactants are at the 4-position, i.e., 4-halophthalic anhydride and 4-hydroxyphthalic anhydride, the oxy-diphthalic product will be 4,4'-oxy-diphthalic anhydride, characterized by the formula

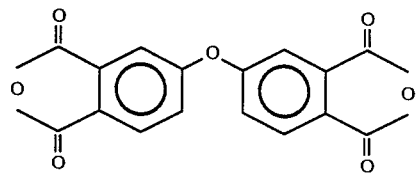

When both reactants are 3-substituted, that is, when the reactants are 3-halophthalic anhydride and 3-hydroxyphthalic anhydride, the oxy-diphthalic product will be 3,3'-oxy-diphthalic anhydride characterized by the formula

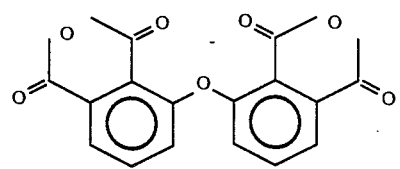

Alternatively, a mixture of 3-substituted and 4-substituted phthalic anhydrides, such as 3-halophthalic anhydride and 4-hydroxyphthalic anhydride or 4-halophthalic anhydride and 3-hydroxyphthalic anhydride may be employed to prepare a 3,4-oxy-diphthalic anhydride of the formula

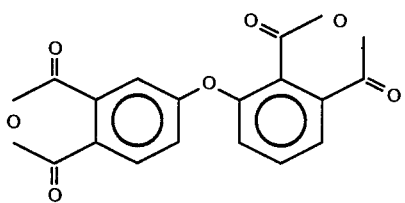

The halogen substituent on the starting halophthalic anhydride reactant may be F, Cl, Br or I. The preferred reactant is fluorophthalic anhydride. It has been found that yield of oxy-diphthalic anhydride is surprisingly higher when fluorophthalic anhydride is employed than when other halophthalic anhydrides are employed as reactants under similar reaction conditions.

The alkali metal compound may be potassium fluoride, cesium fluoride or potassium carbonate. The proportions of reactants may vary considerably, however, it is recommended that the alkali metal compound be employed in sufficient proportions to provide at least about one equivalent of potassium (or cesium) per mole of halo-phthalic anhydride. When chloro-phthalic anhydride or bromo-phthalic anhydride reactants are employed together with potassium fluoride or cesium fluoride, it has been found efficacious to provide at least about two equivalents of alkali metal per mole of chloro- or bromo-phthalic anhydride. Preferably the alkali metal compound is employed in substantial excess, for example, up to about 50 percent excess, of the aforesaid equivalent proportions. Furthermore, it is recommended that the reaction be carried out under anhydrous conditions, to minimize the occurrence of undesired side reactions.

The process of the invention is preferably carried out at atmospheric pressure, but super-atmospheric pressure, for example, under autogeneous conditions, may be employed, if desired. The process is preferably carried out in the presence of a polar, aprotic solvent such as N-methyl-pyrrolidone, dimethyl formamide, dimethyl acetamide, triglyme, sulfolane, or the like.

The temperature at which the process is carried out may vary considerably, but will generally be within the range of about 120° to about 220° Celsius. Higher or lower temperature may be employed but are less efficient. The choice of solvent may govern the temperature employed. For example, at atmospheric conditions the boiling point of the solvent becomes a limiting condition. Moreover, the decrease in efficiency of the reaction as the temperature is lowered, varies somewhat with the solvent. For example, the preferred temperature, when using sulfolane as the solvent, is in the range of about 170°–215° and, most preferably, about 180°–190° Celsius.

The following examples are provided to further illustrate this invention and the manner in which it may be carried out. It will be understood, however, that the specific details given in the examples have been chosen for purposes of illustration only and are not to be construed as limiting the invention. In the examples, unless otherwise indicated, all parts and percentages are by weight and all temperatures are in degrees Celsius.

EXAMPLE 1

To a solution of 100 parts of 4-fluorophthalic anhydride and 100 parts of 4-hydroxyphthalic anhydride in 500 parts of dry dimethylformamide, was added 69 parts of potassium carbonate. The mixture was heated to 135° to 140° C. and maintained thereat, with stirring, in an atmosphere of nitrogen, for three hours. The reaction was monitored by gas chromatographic analysis with the following results (shown in GC area percent):

|  | Oxy-Diphthalic Anhydride (G. C. Area %) |
| --- | --- |
| Initial | — |
| After 1 hour | 67.6 |
| After 2 hours | 81.3 |
| After 3 hours | 81.7 |

EXAMPLE 2

Following the general procedure of the preceding example, 5.5 parts of 4-chloro-phthalic anhydride and 5.0 parts of 4-hydroxyphthalic anhydride were dissolved in 100 parts of anhydrous dimethyl formamide. To the solution was added 3.2 parts of potassium carbonate. The mixture was heated and maintained at about 130° to 145°, with stirring, in a dry, inert atmosphere (nitrogen) for about three hours. Analysis of the reaction mixture by gas chromatography indicated 5.5 percent (GC area percent) of 4,4'-oxy-diphthalic anhydride.

EXAMPLE 3

To a solution of 0.66 parts of 4-hydroxyphthalic anhydride and 0.70 parts of 4-fluorophthalic anhydride in 3.8 parts of anhydrous sulfolane, was added 0.23 parts of potassium fluoride. The mixture was heated and maintained at about 180° to 185° C. under a nitrogen atmosphere for four hours. Analysis of the reaction mixture by gas chromatography indicated 92.6 percent (GC area percent) of 4,4'-oxy-diphthalic anhydride.

EXAMPLE 4

A mixture of 0.5 parts of potassium carbonate in 7.2 parts of sulfolane was heated to 205° C. To the mixture was added a solution of 0.32 parts of 4-bromophthalic anhydride and 0.23 parts of 4-hydroxyphthalic anhydride in 4.1 parts of sulfolane. The temperature of the reaction mixture was maintained at about 205°–215° C. for about 4.5 hours. Analysis of the reaction mixture by gas chromatography indicated 7.0 percent (GC area percent) of 4,4'oxy-diphthalic anhydride.

What is claimed is:

1. A process for the preparation of a diphthalic ether dianhydride of the formula

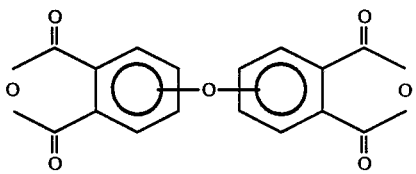

comprising reacting a halo-phthalic anhydride of the formula

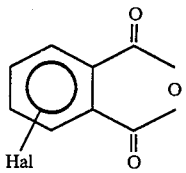

where Hal is F, Cl, Br, or I with an hydroxyphthalic anhydride of the formula

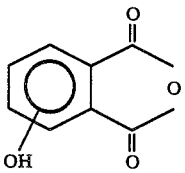

in the presence of a polar, aprotic solvent and an alkali metal compound selected from the group consisting of KF, CsF and $K_2CO_3$.

2. A process according to claim 1 wherein the halophthalic anhydride is fluorophthalic anhydride.

3. A process according to claim 1 wherein the halophthalic anhydride is chlorophthalic anhydride.

4. A process according to claim 1 wherein the halophthalic anhydride is bromophthalic anhydride.

5. A process according to claim 1 wherein the alkali metal compound is potassium carbonate.

6. A process according to claim 1 wherein the alkali metal compound is potassium fluoride.

7. A process according to claim 1 wherein the solvent is selected from the group consisting of sulfolane, N,N-dimethylformamide, N,N-dimethylacetamide, and N-methyl-2-pyrrolidone.

8. A process for the preparation of 4,4'-oxy-diphthalic anhydride which comprises reacting a 4-halophthalic anhydride with 4-hydroxyphthalic anhydride in the presence of a polar, aprotic solvent and an alkali metal compound selected from the group consisting of potassium fluoride, cesium fluoride and potassium carbonate.

9. A process according to claim 8 wherein the 4-halophthalic anhydride is 4-fluorophthalic anhydride.

10. A process according to claim 9 wherein the alkali metal compound is potassium fluoride.

11. A process according to claim 9 wherein the alkali metal compound is potassium carbonate.

12. A process according to claim 8 wherein the 4-halophthalic anhydride is 4-chlorophthalic anhydride.

13. A process according to claim 12 wherein the alkali metal compound is potassium carbonate.

14. A process according to claim 8 wherein the 4-halophthalic anhydride is 4-bromophthalic anhydride.

15. A process according to claim 14 wherein the alkali metal compound is potassium carbonate.

16. A process according to claim 8 wherein the solvent is selected from the group consisting of sulfolane, N,N-dimethylacetamide, N,N-dimethylformamide, and N-methyl-2-pyrrolidone.

17. A process according to claim 8 carried out at a temperature of about 170° to about 215° Celsius.

18. A process for the preparation of 4,4'-oxy-diphthalic anhydride comprising reacting a 4-halo-phthalic anhydride wherein halo- is fluoro-, chloro-, or bromo- with 4-hydroxyphthalic anhydride in the presence of an alkali metal compound selected from the group consisting of KF, CsF, and $K_2CO_3$ and in the presence of a polar, aprotic solvent, selected from the group consisting of sulfolane, N,N-dimethyl formamide, N,N-dimethylacetamide, triglyme, and N-methyl-2-pyrrolidone at a temperature of about 150° to about 210° Celsius.

19. A process for the preparation of 4,4'-oxy-diphthalic anhydride comprising reacting 4-fluoro-phthalic anhydride with 4-hydroxyphthalic anhydride in the presence of potassium carbonate and in the presence of a polar aprotic solvent selected from sulfolane, N,N-dimethyl formamide, N,N-dimethylacetamide, triglyme, and N-methyl-2-pyrrolidone at a temperature of about 120° to about 220° Celsius.

* * * * *